United States Patent [19]

Hirsch et al.

[11] Patent Number: 4,767,770

[45] Date of Patent: * Aug. 30, 1988

[54] METHOD OF INHIBITING AROMATASE

[75] Inventors: Kenneth S. Hirsch, New Palestine; Harold M. Taylor, Indianapolis, both of Ind.

[73] Assignee: Eli Lilly and Company, Indianapolis, Ind.

[*] Notice: The portion of the term of this patent subsequent to Nov. 12, 2002 has been disclaimed.

[21] Appl. No.: 621,416

[22] Filed: Jun. 18, 1984

[51] Int. Cl.$^4$ .................. A61K 31/44; A61K 31/54; A61K 31/495; A61K 31/505
[52] U.S. Cl. .................. 514/342; 514/255; 514/256; 514/320; 514/340; 514/377; 514/227.2; 514/228.8
[58] Field of Search .............. 424/250, 251, 263, 246, 424/248.52, 248.56; 514/226, 232, 237, 255, 256, 340, 342, 320, 377

[56] References Cited

U.S. PATENT DOCUMENTS 3,681,367  8/1972  Lee .................. 260/295 AM

FOREIGN PATENT DOCUMENTS 2504252  8/1975  Fed. Rep. of Germany .

OTHER PUBLICATIONS

Carter et al., Chemotherapy of Cancer, 2nd ed, pp. 361, 364 and 365 (1981).
Lin et al., "The Synthesis of Substituted 2-Aminothiazoles", J. Het. Chem., 16, 377 (1979).

Primary Examiner—Allen J. Robinson
Attorney, Agent, or Firm—Robert A. Conrad; Leroy Whitaker

[57] ABSTRACT

This invention provides a method of inhibiting aromatase and treating or preventing estrogen-dependent diseases in mammals by administering certain amine derivatives. Pharmaceutical formulations of the compounds are also provided.

16 Claims, No Drawings

METHOD OF INHIBITING AROMATASE

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research, supra*.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide pharmaceutical formulations and a method of employing certain amine derivatives inhibiting the enzyme aromatase in mammals. The invention thus provides for the treatment or prevention of breast cancer and other estrogen-dependent diseases.

SUMMARY OF THE INVENTION

This invention provides a method of inhibiting aromatase in mammals which comprises administering an aromatase inhibiting amount of a compound of the formula

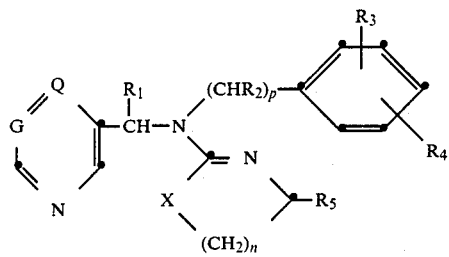

where
G and Q are independently CH or N, provided that they may not both be N at the same time;
$R_1$ is hydrogen or methyl;
p is 0, 1, or 2;
each $R_2$ is independently hydrogen or methyl;
$R_3$ and $R_4$ are independently hydrogen, halo, trifluoromethyl, nitro, $C_1$–$C_4$ alkyl, or ($C_1$–$C_4$ alkyl)-Z-, where Z is oxygen or sulfur;
X is O or S;
$R_5$ is hydrogen or methyl; and
n is 1 or 2,
or a pharmaceutically acceptable salt thereof.

By virtue of their ability to inhibit the enzyme aromatase, the compounds of formula I are useful in the treatment and prevention of estrogen-dependent diseases, especialy breast cancer, in mammals.

A further aspect of this invention is a pharmaceutical formulation comprising one or more of the compounds of formula I in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

The term "$C_1$–$C_4$ alkyl" refers to branched and straight chain aliphatic radicals of one to four carbon atoms such as methyl, ethyl, propyl, isopropyl, butyl, tert-butyl, and the like. The term "halo" refers to fluoro, chloro, bromo, and iodo.

A preferred group of compounds useful in this invention are those wherein:
(a) G and Q are both CH,
(b) $R_1$ is hydrogen,
(c) p is 0 or 1,
(d) at least one of $R_3$ and $R_4$ is halo, especially fluoro or chloro, preferably in the para-position,
(e) n is 1, and
(f) X is S.

The compounds used in this invention and methods of making the compounds are disclosed in copending U.S. patent application Ser. No. 472,439, filed Mar. 7, 1983. The compounds as disclosed in the application are described as being useful as plant fungicides and plant growth regulators. The application does not disclose any utility for use in humans or any utility related to the inhibition of aromatase or treatment of estrogen-dependent diseases.

The compounds of formula I may be prepared by methods employing known starting materials that are readily available. The disubstituted amine that is employed as a starting material can be prepared by reacting an appropriately substituted amine with a carbonyl derivative to form a Schiff base, and then reducing the Schiff base by known procedures, preferably by a palladium on carbon catalyzed hydrogenation reaction or by using sodium borohydride in alcohol. This amine starting material may also be prepared by reacting a primary amine with a halogen derivative again according to standard procedures. The schemes for these reactions are as follows:

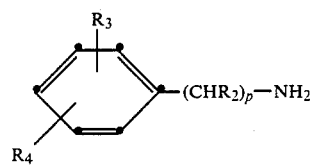

-continued

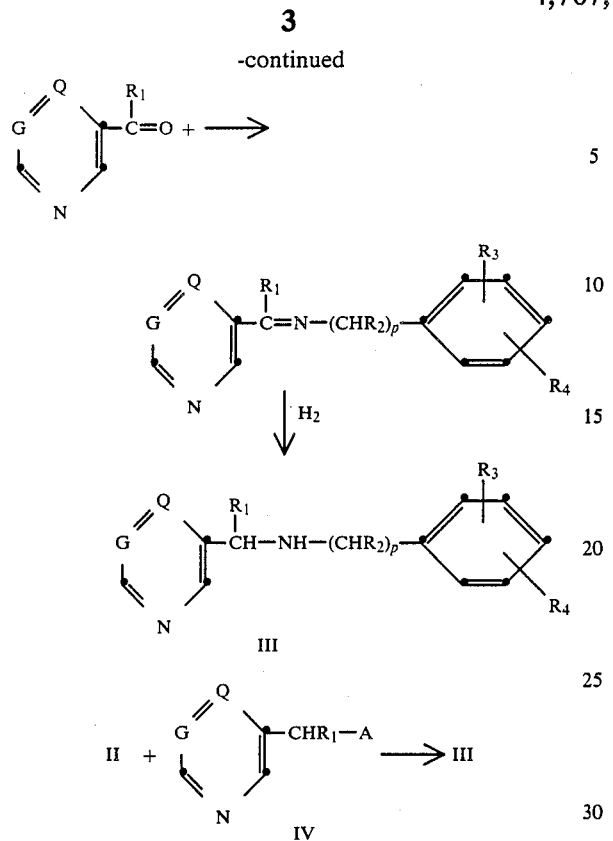

wherein A is a good leaving group such as halogen.

For compounds of formula I where $R_1$ is hydrogen, the starting amine may be prepared by acylating an appropriate primary amine to provide the corresponding amide which is reduced to the secondary amine starting material. The scheme for this reaction is as follows:

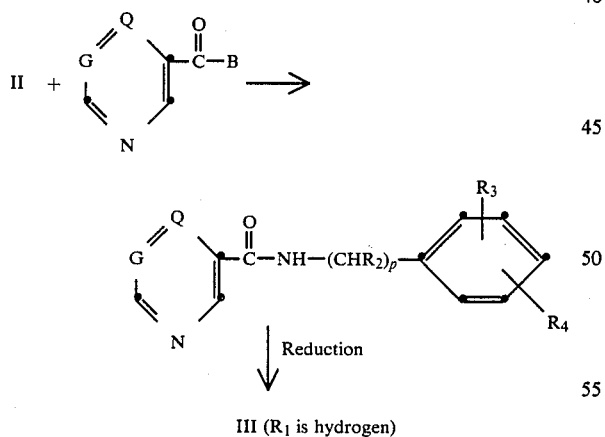

wherein B is a good leaving group such as halogen, $-O-(C_1-C_4$ alkyl) or

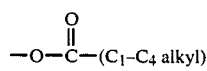

and the like.

The compounds of formula I may be prepared by procedures well known to those skilled in the art. The preferred synthetic process involves reacting the disubstituted amine starting material, or its alkali metal derivative, with an appropriate isocyanate or isothiocyanate analog to give a compound of formula I. The scheme for this reaction is as follows:

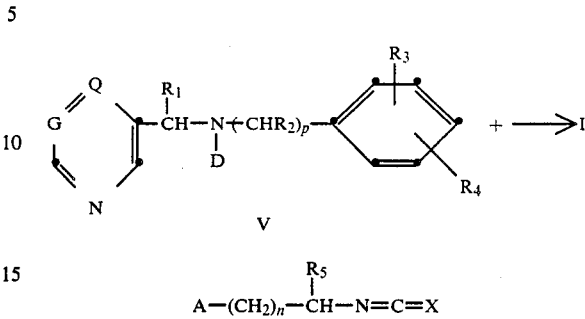

wherein A is halogen and D is hydrogen or an alkali metal such as sodium or lithium. This procedure is generally carried out by reacting approximately equimolar quantities of the amine and isothiocyanate or isocyanate analogs in an aprotic solvent and at a temperature in the range of from about 0° C. to about 150° C. The preferred temperature range is from about 25° C. to the reflux temperature of the reaction mixture. A base such as triethylamine is preferably added to the mixture to promote the reaction process when D is hydrogen in the above reaction scheme. Suitable aprotic solvents include ethyl acetate, chloroform, dichloromethane, benzene and the like. Chloroform and ethyl acetate are preferred. The product is usually formed after about 1 hour to about 3 days depending on the specific reactants involved. The reaction mixture is then worked up according to procedures well known in the art. Typically, either the solid is filtered off and the filtrate is evaporated under reduced pressure or the reaction mixture is diluted with water and the organic phase separated, dried and concentrated under vacuum. If desired, the product may then be further purified by standard procedures such as crystallization or column chromatography over silica gel.

When $R_5$ is methyl, another similar process which may be used to prepare compounds of formula I involves reacting the disubstituted amine starting material with an alkene isocyanate or isothiocyanate derivative to provide a urea derivative, which can then be cyclized in acid according to the following reaction scheme:

III + CH$_2$=CH—(CH$_2$)$_n$—N=C=X $\longrightarrow$

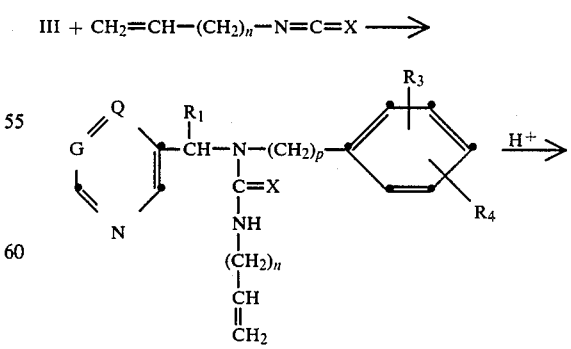

The reaction of the disubstituted amine with the alkene isocyanate or isothiocyanate derivative is performed as outlined above. The cyclization of the compound in acid can also be performed by procedures well known to those skilled in the art. Typical acids suitable for use in this reaction include hydrochloric, hydrobromic, hydriodic and the like. The reaction occurs at a temperature in the range of from about 25° C. to about 200° C., more preferably at about 75° C. to 125° C. After the reaction is complete, which may take from 1 hour to 10 days, the mixture is generally made basic. The product may then be either collected by filtration or extracted with a water immiscible solvent such as chloroform or ethyl acetate. The product may then be further purified if desired by crystallization, column chromatography or other like procedures.

The N-alkali metal derivative of the disubstituted amine starting material described above may also be alkylated directly with the 2-halogen substituted 5- or 6-membered heterocyclic ring as described below.

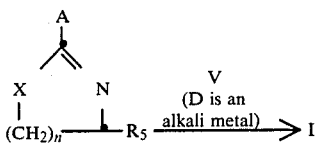

This reaction is typically carried out in a suitable solvent and at a low temperature in an inert atmosphere. Suitable solvents should be water-free and include the aprotic solvents, preferably diethyl ether and tetrahydrofuran. The temperature range of the reaction mixture may be from about 20° C. to −100° C. with 0° C. to −20° C. being preferred. The reaction is substantially complete after 10 minutes to 24 hours. The isolated product may then be purified if desired by standard techniques.

An alternative procedure for preparing the compounds of formula I involves beginning with an appropriately substituted 5- or 6-membered heterocyclic amine. For example, the heterocyclic amine may be directly alkylated in two steps to afford a compound of the invention. The scheme for this reaction is as follows:

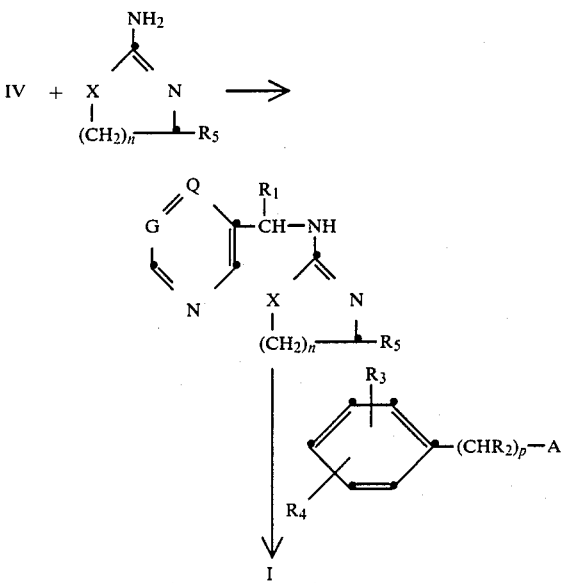

with the proviso that p is other than 0. The procedure used to prepare compounds of the invention by this alternative process involves standard alkylation techniques readily known to those skilled in the art. Either step of the reaction can be carried out by combining approximately equimolar quantities of the starting materials in a mutual solvent such as tetrahydrofuran, diethyl ether, dichloromethane, dioxane, dimethylsulfoxide, dimethylformamide, benzene, toluene and the like. Generally a base is also used in the reaction as an acid scavenger. Commonly used bases include sodium carbonate, potassium carbonate, sodium hydroxide, triethylamine and related bases. The reaction generally is substantially complete after about two to about 200 hours when carried out at a temperature of about 20° to about 200° C., preferably from about 30° to about 100° C. The product of the reaction may be isolated by simply removing the reaction solvent, for instance by evaporation under reduced pressure. Also, the reaction mixture may be added to water and the product collected by filtration or extracted into a water immiscible solvent. The product thus isolated can be further purified if desired by any of several well known techniques.

As will be recognized by those skilled in the art, the compounds of Formula I may contain one or more asymmetric carbon atoms. This invention is not limited to any particular isomer but includes the individual stereoisomers as well as the mixtures of isomers of Formula I.

The pharmaceutically acceptable acid addition salts of the bases represented by the compounds of Formula I can be prepared employing those acids of sufficient acidity to form acid addition salts with the weakly basic nitrogen atoms. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds used in this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-$H_2O$ which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity ($EC_{50}$) when the concentration of substrate (androstenedione) is 0.1 μM. The $EC_{50}$'s of certain of the compounds of formula I are summarized in Table 1.

TABLE 1

Aromatase Inhibition in the Rat Ovarian Microsome Assay

| Compound of Formula I | $EC_{50}$* |
|---|---|
| N—(4-chlorophenyl)-N—(4,5-dihydro-2-thiazolyl)-3-pyridinemethanamine | 0.068 |
| N—(4-chlorophenyl)-N—(4,5-dihydro-4-methyl-2-thiazolyl)-3-pyridinemethanamine | 0.026 |
| N—(4-chlorophenyl)-N—(4,5-dihydro-2-thiazolyl)-α-methyl-3-pyridinemethanamine | 2.350 |
| N—(4-chlorophenyl)-5,6-dihydro-N—(3-pyridylmethyl)-4H—1,3-thiazin-2-amine | 0.072 |
| N—(4,5-dihydro-2-thiazolyl)-N—[4-(methylthio)phenyl]-3-pyridinemethanamine | 3.2 |
| N—(4,5-dihydro-2-thiazolyl)-N—phenyl-3-pyridinemethanamine | 0.46 |
| N—(4,5-dihydro-2-thiazolyl)-N—(4-bromophenyl)-3-pyridinemethanamine | 0.110 |
| N—(4,5-dihydro-2-thiazolyl)-N—(2,4-dichlorobenzyl)-3-pyridinemethanamine | 0.118 |
| N—(4-chlorophenyl)-N—(4,5-dihydro-4-methyl-2-thiazolyl)-α-methyl-3-pyridinemethanamine | 1.95 |
| N—(2,4-difluorophenyl)-N—(4,5-dihydro-2-thiazolyl)-3-pyridinemethanamine | 0.028 |
| N—(4-chlorophenyl)-N—(4,5-dihydro-2-thiazolyl)-5-pyrimidinemethanamine | 0.61 |
| N—(4-chlorophenyl)-N—(4,5-dihydro-2-thiazolyl)-2-pyrazinemethanamine | 3.13 |
| N—[1-(4-chlorophenyl)ethyl]-N—(4,5-dihydro-2-thiazolyl)-3-pyridinemethanamine | 0.048 |
| N—(4,5-dihydro-2-thiazolyl)-N—[1-(4-fluorophenyl)ethyl]-α-methyl-3-pyridinemethanamine | 3.3 |
| N—(4,5-dihydro-2-thiazolyl)-N—[2-(4-chlorophenyl)ethyl]-3-pyridinemethanamine | 0.90 |
| N—(4-chloro-2-methylphenyl)-N—(4,5-dihydro-2-thiazolyl)-3-pyridinemethanamine | 0.44 |
| N—(4-chlorophenyl)-N—(4,5-dihydro-2-oxazolyl)-3-pyridinemethanamine | 0.080 |

*Concentration of compound in μM required to achieve 50% inhibition of aromatase activity when substrate concentration is 0.1 μM.

By virtue of their ability to inhibit the enzyme aromatase, the compounds employed in the method of this invention are able to inhibit the synthesis of estrogens in mammals, thereby making the compounds useful in the treatment of estrogen-dependent diseases, such as breast cancer. This in vivo activity was demonstrated in the following test systems.

Estrogen Synthesis Inhibition in Rats

Immature female Wistar rats (45–55 grams) were divided into control and test groups of 2–8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol. After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM $MgCl_2 \cdot 6H_2O$, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

TABLE 2

Effects of Compounds of Formula I on Estrogen Levels and Uterine Weight

| Test No. | Compound | Dose* | Animals | Mean Uterine Weight (mg) | Mean Steroid Concentration** estradiol | estrone | estriol |
|---|---|---|---|---|---|---|---|
| I | N—(4-chlorophenyl)-N—(4,5-dihydro-2-thiazolyl)-3-pyridinemethanamine | 30 | 4 | 141.5+ | 1.46 | 0.31 | 0.27 |
|  |  | 300 | 5 | 136.0+ | 1.42 | 0.09 | 0.46 |
|  | Testosterone-treated control | — | 8 | 211.5 | 1.43 | 0.10 | 0.24 |
|  | Corn oil control | — | 6 | 47.7+ | — | — | — |
| II | N—(2,4-difluorophenyl)-N—(4,5-dihydro-2-thiazolyl)-3-pyridinemethanamine | 30 | 4 | 140.0 | 1.27 | 0.65 | 1.56 |
|  |  | 300 | 4 | 104.5+ | 1.05+ | 0.31+ | 1.18 |
|  | Testosterone-treated control | — | 6 | 176.7 | 2.07 | 0.64 | 1.98 |
|  | Corn oil control | — | 4 | 51.8+ | — | — | — |
| III | N—(4-chlorophenyl)-N—(4,5-dihydro-4-methyl-2-thiazolyl)-3-pyridinemethanamine | 30 | 4 | 225.5 | 2.40 | 1.14 | 1.56 |
|  |  | 300 | 5 | 187.6 | 0.95 | 0.62 | 0.37 |
|  | Testosterone-treated control | — | 8 | 220.0 | 1.31 | 1.02 | 1.32 |
|  | Corn oil control | — | 2 | 157.0+ | — | — | — |
| IV | N—(4-chlorophenyl)-5,6-dihydro-N—(3-pyridylmethyl)-4H—1,3-thiazin-2-amine | 200 | 5 | 193.0 | 1.54 | 0.11 | 0.04 |
|  | N—[1-(4-chlorophenyl)-ethyl]-N—(4,5-dihydro-2-thiazolyl)-3-pyridinemethanamine | 200 | 5 | 185.8 | 1.01 | 0.13 | 0.04 |
|  | testosterone-treated control | — | 8 | 213.5 | 1.98 | 0.24 | 0.14 |
|  | Corn oil control | — | 4 | 145.3+ | — | — | — |

*ppm in feed. 300 ppm corresponds to approximately 30 mg/kg/day; 200 ppm corresponds to approximately 20 mg/kg/day; 30 ppm corresponds to approximately 3 mg/kg/day.
**femtomoles per milligram of protein.
+significantly different from testosterone-treated control, $p < 0.05$.

DMBA-induced Mammary Tumor Inhibition

Mammary tumors were produced in female Sprague-Dawley rats which were 50–60 days old by the gavage administration of 20 mg of 7,12-dimethylbenz[a]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any other group. Each control and test group contained 8 animals. The test compound was administered mixed into the food at a concentration of 300 ppm (corresponding to an appropriate daily dose of 30 mg/kg). Every experiment included a group of control rats having tumors and were given food without the compound admixed. The tumors were measured at the start of the experiments and generally had an area of approximately 15–100 mm². The area of each tumor was calculated by multiplying the shortest and longest diameters of the tumor. The treatment and measurement of animals continued for 4–5 weeks at which time the final areas of the tumors were determined. For each compound (and control) at each dose level, the change in the mean tumor area was determined. The results of these tests are shown in Table 3 below.

Test 3
Anti-Tumor Activity

| Test No. | Compound | Dose* | Duration of test (weeks) | Mean Tumor Area (mm²) Start | Finish |
|---|---|---|---|---|---|
| I | Control | — | 5 | 73.9 | 1140.0 |
|  | N—(2,4-difluorophenyl)-N—(4,5-dihydro-2-thiazolyl)-3-pyridinemethanamine | 300 ppm | 5 | 83.6 | 536.0 |
| II | Control | — | 4 | 62.8 | 1087.0 |
|  | N—(4-chlorophenyl)-N—(4,5-dihydro-2-thiazolyl)-3-pyridinemethamine | 300 ppm | 4 | 61.4 | 464.0 |

*dosed in the diet. 300 ppm corresponds to approximately 30 mg/kg/day.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of Formula I.

Accordingly, the invention includes a pharmaceutical composition comprising as active ingredient a compound of formula I associated with a pharmaceutically acceptable carrier. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions of the invention may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of formula I.

EXAMPLE 1

Hard gelatin capsules are prepared using the following ingredients:

|  | per capsule |
|---|---|
| N—(4-trifluoromethylphenyl)-N—(4,5-dihydro-2-oxazolyl)-3-pyridinemethanamine | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 2

Capsules each containing 20 mg of medicament are made as follows:

|  | per capsule |
|---|---|
| N—(3-methyl-4-fluorophenyl)-5,6-dihydro-N—(2-pyrazinylmethyl)-4H—1,3-thiazine-2-amine | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 3

Capsules each containing 100 mg of active ingredient are made as follows:

|  | per capsule |
|---|---|
| N—(4-nitrophenyl)-N—(4,5-dihydro-2-oxazolyl)-5-pyrimidinemethanamine | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 4

Tablets each containing 10 mg of active ingredient are made up as follows:

|  | per tablet |
|---|---|
| N—(4-bromophenyl)-5,6-dihydro-N—(5-pyrimidinylmethyl)-4H—1,3-oxazin-2-amine | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 5

A tablet formula is prepared using the ingredients below:

|  | per tablet |
|---|---|
| N—[1-(4-isopropoxyphenyl)-ethyl]-N—(4,5-dihydro-4-methyl-2-thiazolyl)-3-pyridinemethanamine | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 6

Suppositories each containing 25 mg of active ingredient are made as follows:

|  | per suppository |
|---|---|
| N—(4-butylphenyl)-N—(4,5-dihydro-4-methyl-2-oxazolyl)-α-methyl-2-pyrazinemethanamine | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 5 mg of medicament per 5 ml dose are made as follows:

|  | per 5 ml of suspension |
|---|---|
| N—(4-fluorophenyl)-5,6-dihydro-N—(3-pyridinylmethyl)-4H—1,3-thiazin-2-amine | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 8

An aerosol solution is prepared containing the following components:

|  | Weight % |
|---|---|
| N—(4-trifluoromethylbenzyl)-N—(4,5-dihydro-2-oxazolyl)-α-methyl-5-pyrimidinemethanamine | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula

[Chemical structure]

where
G and Q are independently CH or N, provided that they may not both be N at the same time;
$R_1$ is hydrogen or methyl;
is 0, 1, or 2;
each $R_2$ is independently hydrogen or methyl;
$R_3$ and $R_4$ are independently hydrogen, halo, trifluoromethyl, nitro, $C_1$-$C_4$ alkyl, or ($C_1$-$C_4$ alkyl)-Z-, where Z is oxygen or sulfur;
X is O or S;
$R_5$ is hydrogen or methyl; and
n is 1 or 2,
or a pharmaceutically acceptable salt thereof.

2. The method according to claim 1 employing a compound wherein G and Q are each CH.

3. The method according to claim 2 employing a compound wherein $R_1$ is hydrogen.

4. The method according to claim 3 employing a compound wherein one of $R_3$ and $R_4$ is chloro or fluoro in the para-position.

5. The method according to claim 4 employing N-(4-chlorophenyl)-N-(4,5-dihydro-2-thiazolyl)-3-pyridinemethanamine or a pharmaceutically acceptable salt thereof.

6. The method according to claim 4 employing N-(4-chlorophenyl)-N-(4,5-dihydro-4-methyl-2-thiazolyl)-3-pyridinemethanamine or a pharmaceutically acceptable salt thereof.

7. The method according to claim 4 employing N-(2,4-difluorophenyl)-N-(4,5-dihydro-2-thiazolyl)-3- pyridinemethanamine or a pharmaceutically acceptable salt thereof.

8. A method of preventing or treating estrogen-dependent diseases in a mammal which comprises administering to said mammal an effective amount of a compound according to the formula

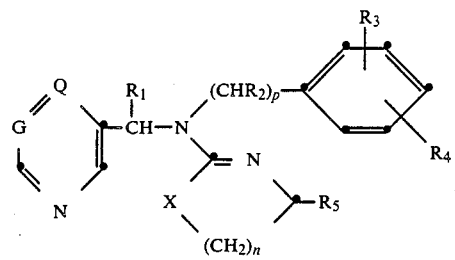

where
G and Q are independently CH or N, provided that they may not both be N at the same time;
$R_1$ is hydrogen or methyl;
p is 0, 1, or 2;
each $R_2$ is independently hydrogen or methyl;
$R_3$ and $R_4$ are independently hydrogen, halo, trifluoromethyl, nitro, $C_1$-$C_4$ alkyl, or ($C_1$-$C_4$ alkyl)-Z-, where Z is oxygen or sulfur;
X is O or S;
$R_5$ is hydrogen or methyl; and
n is 1 or 2,
or a pharmaceutically acceptable salt thereof.

9. The method according to claim 8 employing a compound wherein G and Q are each CH and $R_1$ is hydrogen.

10. The method according to claim 9 employing a compound wherein one of $R_3$ and $R_4$ is chloro or fluoro in the para-position.

11. The method according to claim 10 employing N-(4-chlorophenyl)-N-(4,5-dihydro-2-thiazolyl)-3-pyridinemethanamine or a pharmaceutically acceptable salt thereof.

12. The method according to claim 10 employing N-(2,4-difluorophenyl)-N-(4,5-dihydro-2-thiazolyl)-3-pyridinemethanamine or a pharmaceutically acceptable salt thereof.

13. The method according to claim 8 wherein the estrogen-dependent disease is breast carcinoma.

14. The method according to claim 13 employing a compound wherein G and Q are each CH and $R_1$ is hydrogen.

15. The method according to claim 14 employing a compound wherein one of $R_3$ and $R_4$ is chloro or fluoro in the para-position.

16. The method according to claim 15 employing N-(2,4-difluorophenyl)-N-(4,5-dihydro-2-thiazolyl)-3-pyridinemethanamine or a pharmaceutically acceptable salt thereof.

* * * * *

UNITED STATES PATENT AND TRADEMARK OFFICE
CERTIFICATE OF CORRECTION

PATENT NO. : 4,767,770

DATED : August 30, 1988

INVENTOR(S) : Kenneth S. Hirsch et al.

It is certified that error appears in the above-identified patent and that said Letters Patent is hereby corrected as shown below:

In column 14, line 42, "is 0, 1, 2;" should read
--p is 0, 1, or 2;--.

Signed and Sealed this

Fourteenth Day of March, 1989

Attest:

DONALD J. QUIGG

Attesting Officer

Commissioner of Patents and Trademarks